United States Patent
Wang et al.

(10) Patent No.: US 11,257,227 B2
(45) Date of Patent: *Feb. 22, 2022

(54) BRAIN IMAGE NORMALIZATION APPARATUS, BRAIN IMAGE NORMALIZATION METHOD, AND BRAIN IMAGE NORMALIZATION PROGRAM

(71) Applicant: FUJIFILM Corporation, Tokyo (JP)

(72) Inventors: Caihua Wang, Tokyo (JP); Jun Masumoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 55 days.

This patent is subject to a terminal disclaimer.

(21) Appl. No.: 16/776,527

(22) Filed: Jan. 30, 2020

(65) Prior Publication Data
US 2020/0167939 A1    May 28, 2020

Related U.S. Application Data (63) Continuation of application No. PCT/JP2018/020475, filed on May 29, 2018.

(30) Foreign Application Priority Data

Aug. 28, 2017 (JP) .............................. JP2017-163009

(51) Int. Cl.
*G06T 7/33* (2017.01)
*G06T 7/37* (2017.01)
(Continued)

(52) U.S. Cl.
CPC ............ *G06T 7/337* (2017.01); *G06K 9/6202* (2013.01); *G06T 7/0014* (2013.01); *G06T 7/37* (2017.01);
(Continued)

(58) Field of Classification Search
USPC .................................................. 382/128, 131
See application file for complete search history.

(56) References Cited

U.S. PATENT DOCUMENTS

| 6,240,308 | B1 * | 5/2001 | Hardy | ................. | A61N 5/1031 |
| | | | | | 345/420 |
| 7,426,319 | B2 * | 9/2008 | Takahashi | ............. | G06T 3/0075 |
| | | | | | 382/294 |

(Continued)

FOREIGN PATENT DOCUMENTS

| JP | 2013198763 | 10/2013 |
| JP | 2014042684 | 3/2014 |

(Continued)

OTHER PUBLICATIONS

Davatzikos et al. Image Registration Based on Boundary Mapping, Feb. 1996, IEEE Transaction on Medical Imaging, vol. 15, No. 1, (Year: 1996).*

(Continued)

*Primary Examiner* — Ishrat I Sherali
(74) *Attorney, Agent, or Firm* — JCIPRNET (57) ABSTRACT

A brain image normalization apparatus, having a processor configured to: detect at least four reference landmarks of a left eye, a right eye, a diencephalon, a fornix, a corpus callosum, a left hippocampus, and a right hippocampus from a brain image including a brain of a subject; perform registration between the detected reference landmarks and reference landmarks corresponding to the detected reference landmarks included in a standard brain image; and normalize the brain image based on a result of the registration.

20 Claims, 5 Drawing Sheets

(51) Int. Cl.
*G06K 9/62* (2022.01)
*G06T 7/00* (2017.01)
(52) U.S. Cl.
CPC ............... *G06K 2209/051* (2013.01); *G06T 2207/30016* (2013.01)

(56) References Cited

U.S. PATENT DOCUMENTS

| | | | | |
|---|---|---|---|---|
| 7,646,898 | B1* | 1/2010 | Nowinski | G06T 7/33 |
| | | | | 382/128 |
| 7,787,671 | B2* | 8/2010 | De Leon | G06T 7/143 |
| | | | | 382/128 |
| 7,903,849 | B2* | 3/2011 | Kimura | G06T 7/30 |
| | | | | 382/128 |
| 8,041,088 | B2* | 10/2011 | Mallya | A61B 6/032 |
| | | | | 382/128 |
| 8,838,201 | B2* | 9/2014 | Mori | A61B 6/5217 |
| | | | | 600/410 |
| 9,064,332 | B2* | 6/2015 | Hermosillo Valadez | |
| | | | | G06T 11/003 |
| 9,251,596 | B2* | 2/2016 | Rueckert | G06K 9/468 |
| 9,662,083 | B2* | 5/2017 | Sakaue | A61B 6/469 |
| 10,573,414 | B2* | 2/2020 | Kamali-Zare | G06K 9/20 |
| 2006/0233430 | A1 | 10/2006 | Kimura | |
| 2010/0259263 | A1* | 10/2010 | Holland | A61B 5/055 |
| | | | | 324/310 |
| 2013/0102877 | A1* | 4/2013 | Mori | G01R 33/5608 |
| | | | | 600/410 |
| 2015/0294445 | A1 | 10/2015 | Sakaue | |
| 2016/0143573 | A1* | 5/2016 | Brickman | A61B 5/055 |
| | | | | 382/131 |
| 2017/0079581 | A1* | 3/2017 | Walczak | A61B 5/055 |
| 2018/0268942 | A1* | 9/2018 | Kamali-Zare | A61B 5/7278 |
| 2019/0350486 | A1* | 11/2019 | Walczak | A61M 5/14 |
| 2020/0074626 | A1* | 3/2020 | Fan | G06T 7/33 |

FOREIGN PATENT DOCUMENTS

| | | |
|---|---|---|
| JP | 2014225105 | 12/2014 |
| JP | 2015205164 | 11/2015 |

OTHER PUBLICATIONS

Dai et al. aBEAT: A Toolbox for consitent Analysis of Longitudinal Adult Brain MRI, Apr. 2013, PLOS One. vol. 8, Issue 4, (Year 2013).*

Grachev et al., A Method for Assessing the Accuracy of Inter-subject Registration of the Human Brain Using Anatomical Landmarks, Neuro-Image, 1999, Article ID nimg. 1998.0397, http://www.idealibrary.com, pp. 250-268. (Year: 1999).*

"International Search Report (Form PCT/ISA/210) of PCT/JP2018/020475," dated Aug. 7, 2018, with English translation thereof, pp. 1-3.

"Written Opinion of the International Searching Authority (Form PCT/ISA/237) of PCT/JP2018/020475," dated Aug. 7, 2018, with English translation thereof, pp. 1-7.

Saman Sarraf et al., "DeepAD: Alzheimer's Disease Classification via Deep Convolutional Neural Networks using MRI and fMRI", bioRxiv, Aug. 21, 2016, pp. 1-15.

* cited by examiner

BRAIN IMAGE NORMALIZATION APPARATUS, BRAIN IMAGE NORMALIZATION METHOD, AND BRAIN IMAGE NORMALIZATION PROGRAM

CROSS-REFERENCE TO RELATED APPLICATIONS

This application is a Continuation of PCT International Application No. PCT/JP2018/020475 filed on May 29, 2018, which claims priority under 35 U.S.C. § 119(a) to Japanese Patent Application No. 2017-163009 filed on Aug. 28, 2017. Each of the above application(s) is hereby expressly incorporated by reference, in its entirety, into the present application.

BACKGROUND OF THE INVENTION

1. Field of the Invention

The present invention relates to a brain image normalization apparatus, a brain image normalization method, and a non-transitory computer readable medium for storing a brain image normalization program for normalizing a brain image for input to a discriminator that discriminates dementia and the like based on a brain image, for learning of the discriminator, and the like.

2. Description of the Related Art

With the arrival of an aging society, the number of patients with dementia is increasing year by year. Dementia develops in a case where a protein called amyloid β accumulates in the brain and accordingly brain atrophy progresses and cognitive ability declines. Since there is no cure for dementia, it is important in terms of maintaining the quality of life to detect brain atrophy early and start treatment early to delay the progression of dementia.

In order to meet such a demand, in recent years, information regarding the state of the brain can be acquired by nuclear medicine examinations such as single photon emission computed tomography (SPECT) and positron emission tomography (PET), CT images acquired by computerized tomography (CT) apparatuses, and MRI images acquired by magnetic resonance imaging (MRI) apparatuses. For example, decreased blood flow and metabolism in a local part of the brain can be found by checking a temporal change in the local part of the brain using SPECT and PET images.

On the other hand, brain atrophy can be found by calculating the volume of a specific part of the brain using MRI images and comparing a temporal change in the volume. For example, JP2014-042684A has proposed a method of performing registration between two brain images having different imaging dates and times and then dividing each of the two brain images into tissue regions (gray matter and white matter) and acquiring the amount of change for each tissue region.

A method of automatically discriminating between a normal brain image and a brain image of dementia by machine learning has also been proposed (DeepAD: Alzheimer's Disease Classification via Deep Convolutional Neural Networks using MRI and fMRI, Saman Sarrafa et al., first posted online Aug. 21, 2016; doi: http://dx.doi.org/10.1101/070441). For learning of a discriminator that performs such discrimination, a large number of normal brain sample images and sample images of the brain of a dementia patient are used as teacher data.

SUMMARY OF THE INVENTION

In order to improve the discrimination accuracy of the brain using the discriminator described above, it is necessary to normalize sample images used for learning and brain images input for discrimination. In DeepAD: Alzheimer's Disease Classification via Deep Convolutional Neural Networks using MRI and fMRI, Saman Sarrafa et al., first posted online Aug. 21, 2016; doi: http://dx.doi.org/10.1101/070441, the entire brain image as a discrimination target is registrated with a standard brain image, and the affine transformation coefficient is calculated to normalize the brain image. In this manner, the brain image can be normalized so that the shape of the brain image matches the standard brain.

On the other hand, the brain contains various anatomical structures. In addition, anatomical features, such as eyes, are also included in the vicinity of the brain. In the method described in DeepAD: Alzheimer's Disease Classification via Deep Convolutional Neural Networks using MRI and fMRI, Saman Sarrafa et al., first posted online Aug. 21, 2016; doi: http://dx.doi.org/10.1101/070441, the shape of the brain can be normalized. However, it is not possible to normalize the brain and anatomical structures included in the vicinity of the brain.

The present invention has been made in view of the above circumstances, and it is an object of the present invention to enable normalization of the brain and anatomical structures included in the vicinity of the brain.

A brain image normalization apparatus according to the present invention comprises: a landmark detection unit that detects at least four reference landmarks of a left eye, a right eye, a diencephalon, a fornix, a corpus callosum, a left hippocampus, and a right hippocampus from a brain image including a brain of a subject; a registration unit that performs registration between the detected reference landmarks and reference landmarks corresponding to the detected reference landmarks included in a standard brain image; and a normalization unit that normalizes the brain image based on a result of the registration.

"Detecting a reference landmark" may be detecting a reference landmark region itself, that is, all pixel positions in the reference landmark, or may be detecting a specific pixel position in the reference landmark, such as the center of gravity, endpoints, and a contour line in the reference landmark.

In the brain image normalization apparatus according to the present invention, the landmark detection unit may detect the reference landmarks by performing template matching between the brain image and a template including the reference landmarks in the standard brain image.

In the brain image normalization apparatus according to the present invention, the landmark detection unit may further detect at least one local landmark from the brain image based on the registration result, the registration unit may perform further registration between the detected reference landmarks and the detected local landmark and reference landmarks and a local landmark corresponding to the detected reference landmarks and the detected local landmark included in the standard brain image, and the normalization unit may normalize the brain image based on a result of the further registration.

A "local landmark" is a region having a characteristic shape in a brain image, which is different from the reference landmark. Specifically, at least one of characteristic regions, such as a sulcus and a cerebral ventricle included in the brain, can be used as a local landmark.

"Detecting a local landmark" may be detecting a local landmark region itself, that is, all pixel positions in the local landmark, or may be detecting a specific pixel position in the local landmark, such as the center of gravity, endpoints, and a contour line in the local landmark.

In the brain image normalization apparatus according to the present invention, the registration unit may perform the registration by similarity transformation. The registration includes further registration.

In the brain image normalization apparatus according to the present invention, the registration unit may perform the registration by nonlinear transformation. The registration includes further registration.

In the brain image normalization apparatus according to the present invention, the registration unit may perform additional registration between the entire brain image and the entire standard brain image after the registration.

A brain image normalization method according to the present invention comprises: detecting at least four reference landmarks of a left eye, a right eye, a diencephalon, a fornix, a corpus callosum, a left hippocampus, and a right hippocampus from a brain image including a brain of a subject; performing registration between the detected reference landmarks and reference landmarks corresponding to the detected reference landmarks included in a standard brain image; and normalizing the brain image based on a result of the registration.

In addition, a program causing a computer to execute the brain image normalization method according to the present invention may be provided.

Another brain image normalization apparatus according to the present invention comprises: a memory that stores commands to be executed by a computer; and a processor configured to execute the stored commands. The processor executes processing for detecting at least four reference landmarks of a left eye, a right eye, a diencephalon, a fornix, a corpus callosum, a left hippocampus, and a right hippocampus from a brain image including a brain of a subject, performing registration between the detected reference landmarks and reference landmarks corresponding to the detected reference landmarks included in a standard brain image, and normalizing the brain image based on a result of the registration.

According to the present invention, at least four reference landmarks of the left eye, the right eye, the diencephalon, the fornix, the corpus callosum, the left hippocampus, and the right hippocampus are detected from the brain image including the brain of the subject, registration between the detected reference landmarks and reference landmarks corresponding to the detected reference landmarks included in the standard brain image is performed, and the brain image is normalized based on the registration result. For this reason, it is possible to normalize not only the shape of the brain but also at least four anatomical regions of the left eye, the right eye, the diencephalon, the fornix, the corpus callosum, the left hippocampus, and the right hippocampus included in the brain image. Therefore, it is possible to accurately normalize the brain image.

DESCRIPTION OF THE PREFERRED EMBODIMENTS

Figure 1:
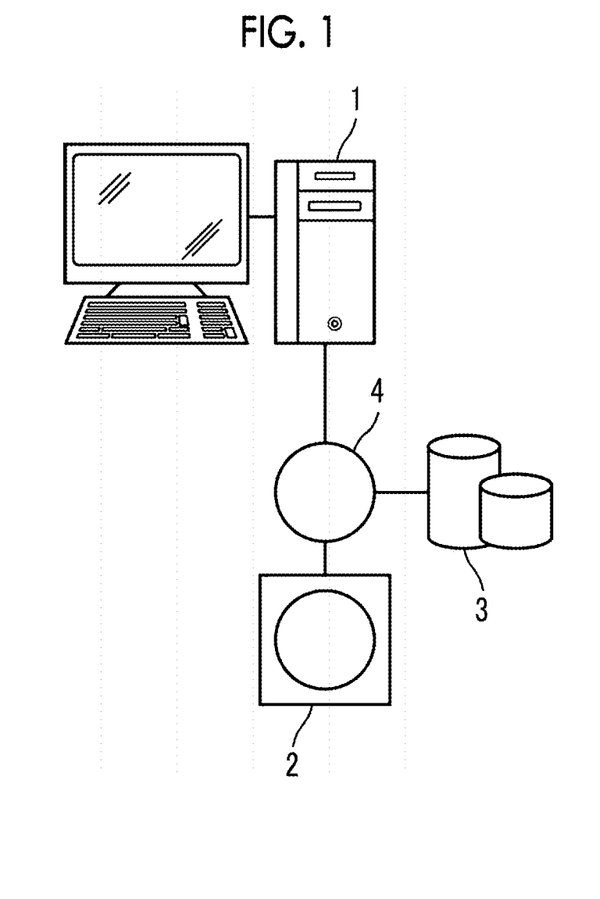
FIG. 1 is a hardware configuration diagram showing an outline of a diagnostic support system to which a brain image normalization apparatus according to an embodiment of the present invention is applied.

Hereinafter, embodiments of the present invention will be described with reference to the accompanying diagrams. FIG. 1 is a hardware configuration diagram showing the outline of a diagnostic support system to which a brain image normalization apparatus according to a first embodiment of the present invention is applied. As shown in FIG. 1, in the diagnostic support system, a brain image normalization apparatus 1 according to the first embodiment, a three-dimensional image capturing apparatus 2, and an image storage server 3 are communicably connected to each other through a network 4.

The three-dimensional image capturing apparatus 2 is an apparatus that generates a three-dimensional medical image showing a part, which is a diagnostic target part of a patient who is a subject, by imaging the part. Specifically, the three-dimensional image capturing apparatus 2 is a CT apparatus, an MRI apparatus, a PET apparatus, or the like. The medical image generated by the three-dimensional image capturing apparatus 2 is transmitted to the image storage server 3 and is stored therein. In the present embodiment, a diagnostic target part of a patient who is a subject is a brain, the three-dimensional image capturing apparatus 2 is an MRI apparatus, and an MRI image of the head including the brain of the subject is generated as a three-dimensional brain image.

The image storage server 3 is a computer that stores and manages various kinds of data, and comprises a large-capacity external storage device and software for database management. The image storage server 3 communicates with other apparatuses through the wired or wireless network 4 to transmit and receive image data or the like. Specifically, the image storage server 3 acquires various kinds of data including image data of the medical image, which is generated by the three-dimensional image capturing apparatus 2, through the network, and stores the acquired data in a recording medium, such as a large-capacity external storage device, to manage the acquired data. The storage format of image data and the communication between devices through the network 4 are based on a protocol, such as a digital imaging and communication in medicine (DICOM). In the present embodiment, it is assumed that image data of a plurality of three-dimensional brain images are stored in the image storage server 3. In addition, it is assumed that image data of a standard brain image to be described later is also stored in the image storage server 3.

The brain image normalization apparatus 1 is realized by installing a brain image normalization program according to an embodiment of the present invention on one computer.

The computer may be a workstation or a personal computer that is directly operated by a doctor who performs diagnosis, or may be a server computer connected to these through a network. The brain image normalization program is distributed in a state in which the brain image normalization program is recorded on a recording medium, such as a digital versatile disc (DVD) or a compact disk read only memory (CD-ROM), and is installed onto the computer from the recording medium. Alternatively, the brain image normalization program is stored in a storage device of a server computer connected to the network or in a network storage so as to be accessible from the outside, and is downloaded and installed onto a computer used by a doctor as necessary.

Figure 2:
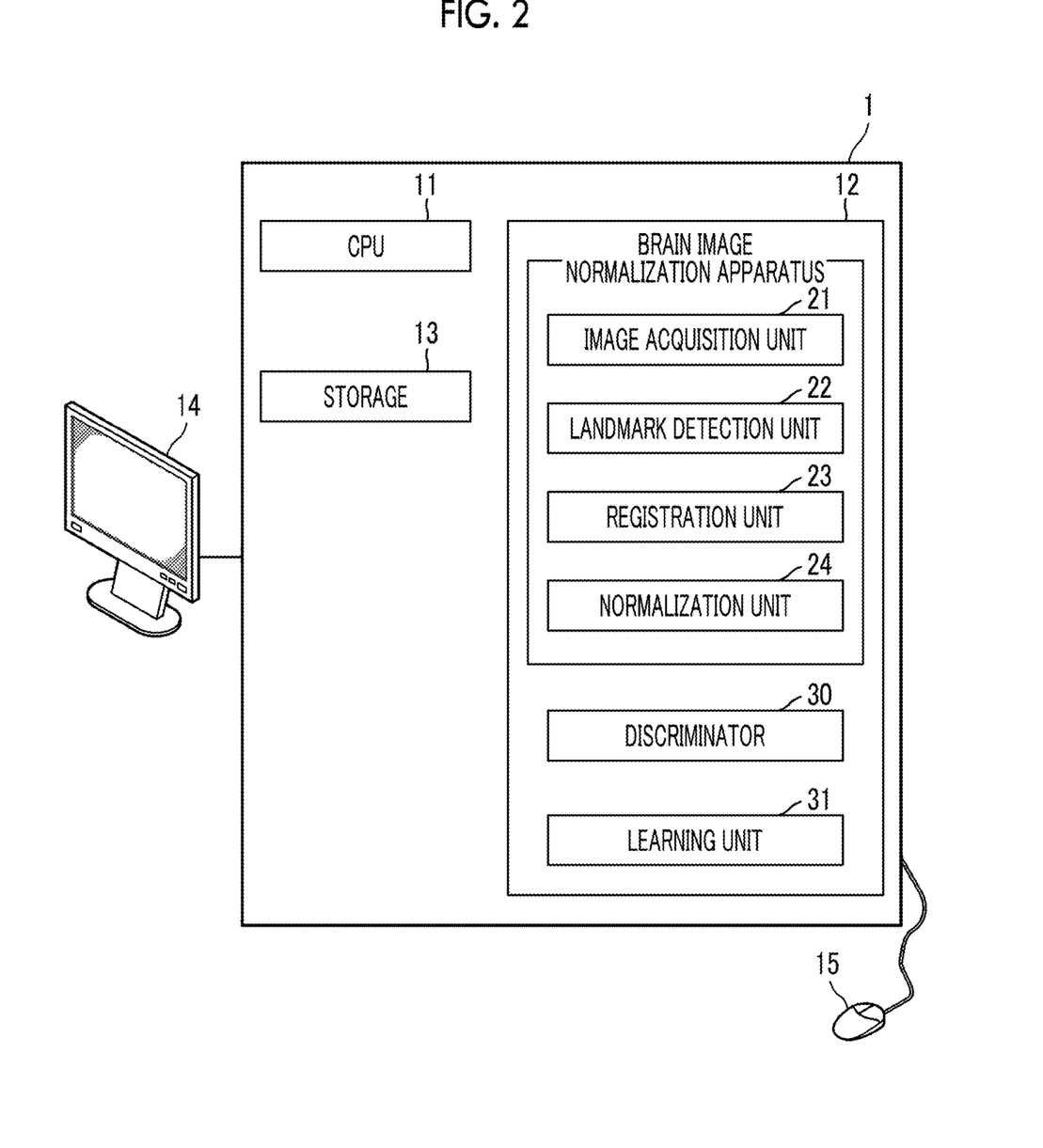
FIG. 2 is a diagram showing the schematic configuration of the brain image normalization apparatus.

FIG. 2 is a diagram showing the schematic configuration of a brain image normalization apparatus realized by installing a brain image normalization program on a computer. As shown in FIG. 2, the brain image normalization apparatus 1 comprises a central processing unit (CPU) 11, a memory 12, and a storage 13 as the configuration of a standard workstation. A display 14, such as a liquid crystal display, and an input unit 15, such as a keyboard and a mouse, are connected to the brain image normalization apparatus 1.

The storage 13 is a storage device, such as a hard disk or a solid state drive (SSD). A brain image B0 of the subject, a standard brain image Bs, and various kinds of information including information required for processing, which are acquired from the image storage server 3 through the network 4, are stored in the storage 13.

Here, the standard brain image Bs is a three-dimensional brain image showing a brain having a standard shape and size and a standard density (pixel value), that is, a standard brain. The standard brain image Bs can be generated by extracting brains from a plurality of brain images, which are acquired by imaging the heads of a plurality of healthy persons with a three-dimensional image capturing apparatus, and averaging the plurality of extracted brains. The standard brain image Bs may be created by computer graphics or the like. Alternatively, a brain image of one healthy person may be used as the standard brain image Bs.

A brain image normalization program is stored in the memory 12. As processing to be executed by the CPU 11, the brain image normalization program defines: image acquisition processing for acquiring the brain image B0 including the brain of the subject; landmark detection processing for detecting at least four reference landmarks of the left eye, the right eye, the diencephalon, the fornix, the corpus callosum, the left hippocampus, and the right hippocampus from the brain image; registration processing for performing registration between the detected reference landmark and a reference landmark corresponding to the detected reference landmark included in the standard brain image Bs; and normalization processing for normalizing the brain image B0 based on the registration result.

Then, the CPU 11 executes these processes according to the program, so that the computer functions as an image acquisition unit 21, a landmark detection unit 22, a registration unit 23, and a normalization unit 24. The brain image normalization apparatus 1 may comprise a plurality of processors or processing circuits that perform image acquisition processing, landmark detection processing, registration processing, and normalization processing.

In the present embodiment, a discrimination program for discriminating whether a brain image is normal or develops dementia using a brain image normalized by the brain image normalization program and a learning program for performing learning of a discriminator using a brain image normalized by the brain image normalization program are installed on the brain image normalization apparatus 1. The CPU 11 also functions as the discriminator 30 and a learning unit 31 by executing discrimination processing and learning processing according to the discrimination program and the learning program.

The image acquisition unit 21 acquires the brain image B0 for normalization from the image storage server 3. In a case where the brain image B0 is already stored in the storage 13, the image acquisition unit 21 may acquire the brain image B0 from the storage 13. In the present embodiment, those stored in the image storage server 3 are brain images acquired by imaging the head of the subject, and include structures other than the brain, such as a skull. The image acquisition unit 21 also acquires a standard brain image Bs from the image storage server 3.

Figure 3:
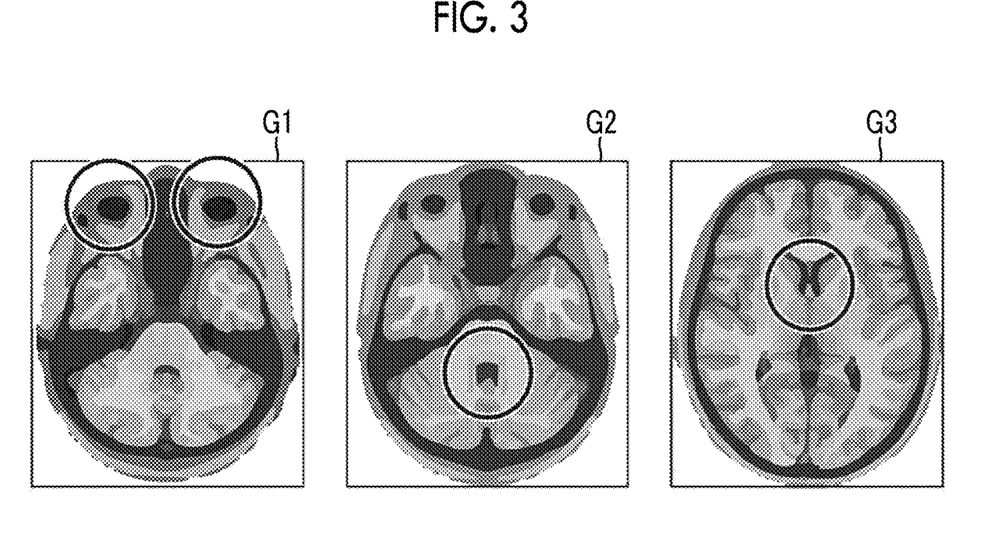
FIG. 3 is a diagram showing slice images on tomographic planes on which the left eye, the right eye, the diencephalon, and the fornix are seen in a brain image.

The landmark detection unit 22 detects at least four reference landmarks among the left eye, the right eye, the diencephalon, the fornix, the corpus callosum, the left hippocampus, and the right hippocampus from the brain image B0. In the present embodiment, four reference landmarks of the left eye, the right eye, the diencephalon, and the fornix are detected. However, the present invention is not limited thereto as long as at least four reference landmarks of the left eye, the right eye, the diencephalon, the fornix, the corpus callosum, the left hippocampus, and the right hippocampus are detected. FIG. 3 is a diagram showing slice images on tomographic planes on which the left eye, the right eye, the diencephalon, and the fornix are seen in the brain image B0. In FIG. 3, a slice image G1 includes the left eye and the right eye, a slice image G2 includes the diencephalon, and a slice image G3 includes the corpus callosum. The left and right eyes, the diencephalon, and the corpus callosum in the respective slice images G1 to G3 are surrounded with a circle.

Here, in the present embodiment, the position of the center of gravity of the reference landmark is detected. However, the pixel position of at the end of the reference landmark, each pixel position on the contour line, or the like may be detected. In addition, the reference landmark region itself, that is, all pixel positions in the reference landmark may be detected.

For detection of the reference landmark, the landmark detection unit 22 comprises a discriminator that is machine-learned so as to detect each of the left eye, the right eye, the diencephalon, and the fornix. For the machine learning, any method (for example, Ada-Boost) is used. In the standard brain image Bs, it is assumed that the positions of the four reference landmarks of the left eye, the right eye, the diencephalon, and the fornix are already detected and stored in the storage 13.

Here, the detection of the reference landmark may be performed on the three-dimensional brain image B0, but may be performed on the slice image of the brain image B0. In this case, the slice image may be a slice image of any of a sagittal section, a coronal section, and an axial section.

After the reference landmark is detected by the discriminator, template matching may be performed in the peripheral region of the detected reference landmark. In this case, a template obtained by extracting each region of the left eye, the right eye, the diencephalon, and the fornix from the standard brain image Bs is stored in the storage 13. Then, the landmark detection unit 22 performs template matching between each template of the left eye, the right eye, the diencephalon, and the fornix and the peripheral region of the reference landmark detected in the brain image B0. In this manner, the reference landmark in the brain image B0 can be detected more accurately. On the other hand, the reference landmark may be detected only by template matching without using a discriminator.

The registration unit 23 performs registration between the reference landmark detected by the landmark detection unit 22 and the reference landmark corresponding to the detected reference landmark in the standard brain image Bs. Here, it is assumed that the positions of the four reference landmarks detected from the brain image B0 in the brain image B0 are Pt1, Pt2, Pt3, and Pt4 and the positions of the reference landmarks in the standard brain image Bs corresponding to the detected reference landmarks are expressed as Ps1, Ps2, Ps3, and Ps4. In addition, in the following description, it is assumed that Pt1, Pt2, Pt3, and Pt4 are used as reference numerals of the reference landmarks detected from the brain image B0 and Ps1, Ps2, Ps3, and Ps4 are used as reference numerals of the reference landmarks in the standard brain image Bs. The registration unit 23 calculates coefficients of similarity transformation between the reference landmarks Pt1, Pt2, Pt3, and Pt4 in the brain image B0 and the reference landmarks Ps1, Ps2, Ps3, and Ps4 in the standard brain image Bs using the following Expression (1). Expression (1) means calculating a coefficient that minimizes the value in Σ. In Expression (1), the position of the reference landmark in the brain image B0 is indicated by Pti (i=1 to 4), and the position of the reference landmark in the standard brain image Bs is indicated by Psi. In practice, however, the position of the reference landmark in the brain image B0 and the position of the reference landmark in the standard brain image Bs have three-dimensional coordinate values.

$$\sum_{i=1}^{4} (Pti - (S(S_x, S_y, S_z)R(\theta_x, \theta_y, \theta_z)Psi + T(t_x, t_y, t_z))^2 \rightarrow \min \quad \text{[Expression 1]}$$

Here, the coefficients calculated in Expression (1) are $S(s_x, s_y, s_z)$, $R(\theta_x, \theta_y, \theta_z)$, and $T(t_x, t_y, t_z)$. $S(s_x, s_y, s_z)$ is a scaling matrix indicating enlargement and reduction in the x, y, and z directions, $R(\theta_x, \theta_y, \theta_z)$ is a three-dimensional rotation matrix, and $T(t_x, t_y, t_z)$ is a three-dimensional movement matrix.

The normalization unit 24 normalizes the brain image B0 based on the registration result. That is, the brain image B0 is subjected to similarity transformation by the coefficients $S(s_x, s_y, s_z)$, $R(\theta_x, \theta_y, \theta_z)$, and $T(t_x, t_y, t_z)$ calculated by the registration unit 23, thereby generating a normalized brain image Bd0.

Figure 4:
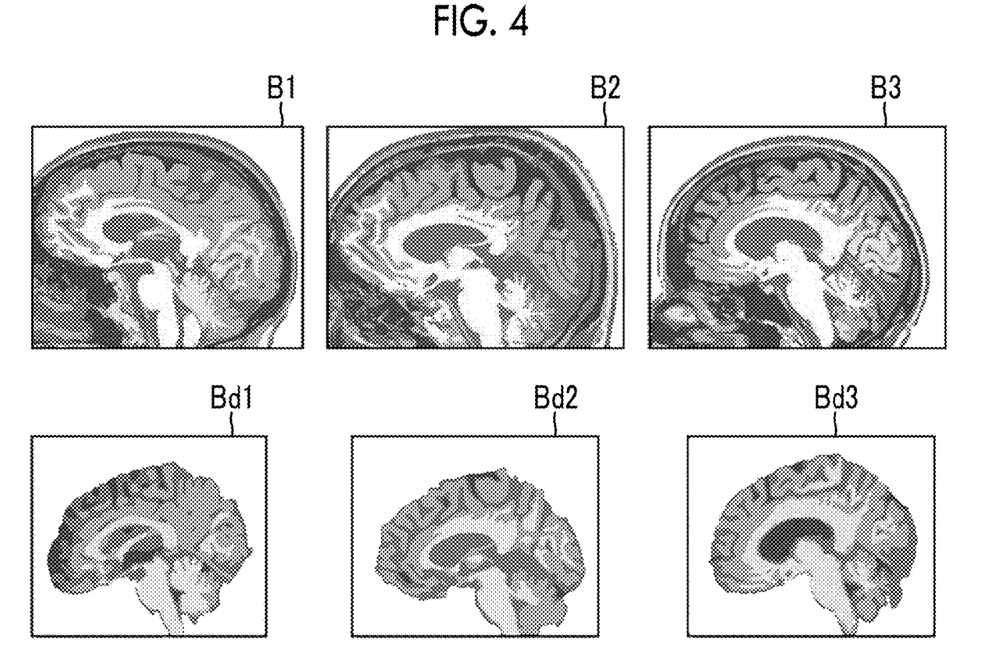
FIG. 4 is a diagram illustrating the normalization of a brain image.

FIG. 4 is a diagram illustrating the normalization of a brain image. As shown in FIG. 4, three normalized brain images Bd1 to Bd3 are generated from the three brain images B1 to B3. The three normalized brain images Bd1 to Bd3 have substantially the same position and the same shape and size as the reference landmarks. In the normalized brain images Bd1 to Bd3 in FIG. 4, only the brain region is extracted. In addition, FIG. 4 shows slice images on the sagittal sections of the brain image and the normalized brain images.

Next, the process performed in the discriminator 30 and the learning unit 31 will be described. In the present embodiment, it is assumed that the discriminator 30 receives the brain image B0 and performs discrimination so as to classify the brain image B0 into three classes of normal, mild dementia, and Alzheimer's disease. For this reason, the discriminator 30 is learned using a plurality of brain images B0 for each class. From the plurality of brain images B0 of each class, a plurality of normalized brain images normalized by the brain image normalization apparatus are generated. The learning unit 31 inputs the normalized brain image of each class to the discriminator 30 and performs the learning of the discriminator 30 so as to output a discrimination result that is a correct answer. As a result, the discriminator 30 that classifies the input brain image into three classes of normal, mild dementia, and Alzheimer's disease is generated. In addition, the discriminator 30 may classify the brain image B0 into two classes of normal and Alzheimer's disease.

Figure 5:
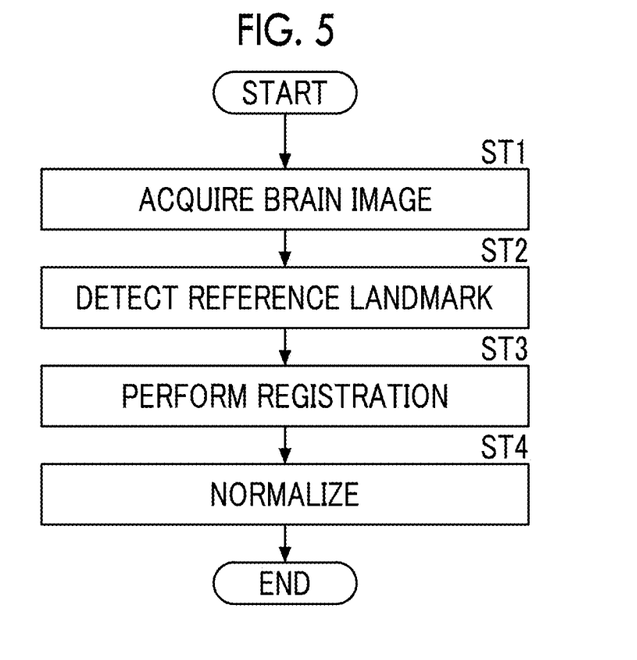
FIG. 5 is a flowchart showing the process performed in a first embodiment.

Next, the process performed in the first embodiment will be described. FIG. 5 is a flowchart showing the process performed in the first embodiment. In the flowchart shown in FIG. 5, the generation of the discriminator 30 and the learning process in the learning unit 31 are omitted. First, the image acquisition unit 21 acquires the brain image B0 to be normalized (step ST1). Then, the landmark detection unit 22 detects at least four reference landmarks among the left eye, the right eye, the diencephalon, the fornix, the corpus callosum, the left hippocampus, and the right hippocampus from the brain image B0 (step ST2).

Then, the registration unit 23 performs registration between the reference landmark detected by the landmark detection unit 22 and the reference landmark corresponding to the detected reference landmark in the standard brain image Bs (step ST3). Then, the normalization unit 24 normalizes the brain image B0 based on the registration result (step ST4), and ends the process.

Thus, according to the first embodiment, at least the four reference landmarks among the left eye, the right eye, the diencephalon, the fornix, the corpus callosum, the left hippocampus, and the right hippocampus are detected from the brain image B0 including the brain of the subject, registration between the detected reference landmark and the reference landmark corresponding to the detected reference landmark included in the standard brain image Bs is performed, and the brain image B0 is normalized based on the registration result. For this reason, it is possible to normalize not only the shape of the brain but also at least four anatomical regions of the left eye, the right eye, the diencephalon, the fornix, the corpus callosum, the left hippocampus, and the right hippocampus included in the brain image B0. Therefore, it is possible to accurately normalize the brain image.

Next, a second embodiment of the present invention will be described. The configuration of a brain image normalization apparatus according to the second embodiment is the same as the configuration of the brain image normalization apparatus according to the first embodiment described above, and only the processing to be performed is different. Accordingly, the detailed description of the apparatus will be omitted herein. The second embodiment is different from the first embodiment in that the landmark detection unit 22 further detects at least one local landmark from the brain image B0 based on the result of registration using the reference landmark and the registration unit 23 performs registration between the reference landmark and the local landmark detected from the brain image B0 and the reference landmark and the local landmark corresponding to the detected reference landmark and local landmark included in the standard brain image Bs.

Figure 6:
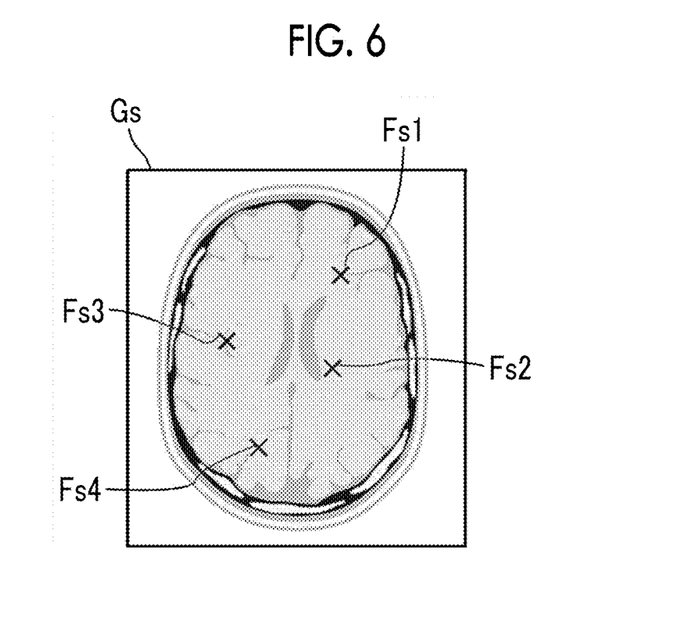
FIG. 6 is a diagram showing a slice image of a standard brain image in which local landmarks are set.

In the second embodiment, the landmark detection unit 22 further detects at least one local landmark different from the reference landmark based on the registration result using the reference landmark in the first embodiment. FIG. 6 is a diagram showing a slice image Gs of the standard brain image Bs for explaining the detection of a local landmark. In the second embodiment, as shown in FIG. 6, local landmarks Fsi other than the left eye, the right eye, diencephalon, the fornix, the corpus callosum, the left hippocampus, and the right hippocampus are set in the standard brain image Bs. As the local landmark Fsi, for example, a sulcus, an end of the sulcus, a cerebral ventricle, and the like can be used. In FIG. 6, four local landmarks Fs1 to Fs4 are set. In the second embodiment, a local region including the local landmark Fsi of the standard brain image Bs is stored in the storage 13 as a template.

In the second embodiment, the landmark detection unit 22 sets the position Fpti of a temporary local landmark corresponding to the local landmark Fsi in the brain image B0 by mapping the local landmark Fsi set in the standard brain image Bs to the brain image B0 based on the following Expression (2) using the result of registration using the reference landmark, that is, the coefficient calculated by the above Expression (1).

$$Fpti = S(S_x, S_y, S_z)R(\theta_x, \theta_y, \theta_z)Fsi + T(t_x, t_y, t_z) \quad \text{[Expression 2]}$$

Then, the landmark detection unit 22 performs template matching between the template of a local region including the local landmark Fsi set in the standard brain image Bs and the peripheral region of the temporary local landmark Fpti set in the brain image B0. As a result, the landmark detection unit 22 detects the accurate position Fti of the local landmark corresponding to the local landmark Fsi. In addition, it is assumed that the reference numeral Fti may also be used for the local landmark in the brain image B0.

Here, the detection of the local landmark Fti may be performed on the three-dimensional brain image B0, but may be performed on the slice image of the brain image B0. In this case, the slice image may be a slice image of any of a sagittal section, a coronal section, and an axial section.

In the second embodiment, the registration unit 23 performs further registration between the reference landmark and the local landmark detected from the brain image B0 and a reference landmark and a local landmark corresponding to the detected reference landmark and local landmark included in the standard brain image Bs. Specifically, using the following Expression (3), coefficients of similarity transformation between the reference landmarks Pt1, Pt2, Pt3, and Pt4 and the local landmark Fti in the brain image B0 and the reference landmarks Ps1, Ps2, Ps3, and Ps4 and the local landmark Fsi in the standard brain image Bs are calculated. Expression (3) means calculating a coefficient that minimizes the sum of values in Σ. Also in Expression (3), the position of the reference landmark in the brain image B0 is indicated Pti, the position of the local landmark in the brain image B0 is indicated by Fti, the position of the reference landmark in the standard brain image Bs is indicated by Psi, and the position of the local landmark in the standard brain image Bs is indicated by Fsi. In practice, however, the position of the reference landmark in the brain image B0, the position of the local landmark in the brain image B0, the position of the reference landmark in the standard brain image Bs, and the position of the local landmark in the standard brain image Bs have three-dimensional coordinate values.

$$\sum_{i=1}^{4}(Pti - \quad \text{[Expression 3]}$$

-continued
$$(S1(S_x, S_y, S_z)R1(\theta_x, \theta_y, \theta_z)Psi + T1(t_x, t_y, t_z))^2 +$$
$$\sum_{i=1}^{n}(Fti -$$
$$(S2(S_x, S_y, S_z)R2(\theta_x, \theta_y, \theta_z)Fsi + T2(t_x, t_y, t_z))^2$$
$$\to \min$$

Here, the coefficients calculated in Expression (3) are $S1(s_x, s_y, s_z)$, $R1(\theta_x, \theta_y, \theta_r)$, $T1(t_x, t_y, t_z)$, $S2(s_x, s_y, s_z)$, $R2(\theta_x, \theta_y, \theta_z)$, and $T2(t_x, t_y, t_z)$. $S1(s_x, s_y, s_z)$ is a scaling matrix indicating enlargement and reduction in the x, y, and z directions for the reference landmark, $R1(\theta_x, \theta_y, \theta_z)$ is a three-dimensional rotation matrix for the reference landmark, and $T1(t_x, t_y, t_z)$ is a three-dimensional movement matrix for the reference landmark. $S2(s_x, s_y, s_z)$ is a scaling matrix indicating enlargement and reduction in the x, y, and z directions for the local landmark, $R2(\theta_x, \theta_y, \theta_z)$ is a three-dimensional rotation matrix for the local landmark, and $T2(t_x, t_y, t_z)$ is a three-dimensional movement matrix for the local landmark. In the first and second embodiments, in order to accurately calculate the scaling matrix S indicating enlargement and reduction in the x, y, and z directions, the rotation matrix R, and the movement matrix T, at least four reference landmarks are required. In a case where there are three reference landmarks, for example, a scaling matrix indicating enlargement and reduction in the normal direction with respect to the plane formed by the three reference landmarks is not accurately determined, and the accuracy of normalization to be described later is reduced. In addition, these at least four reference landmarks should not be on the same plane at the same time.

In the second embodiment, the normalization unit 24 normalizes the brain image B0 based on the result of further registration. That is, the brain image B0 is subjected to similarity transformation by the coefficients $S1(s_x, s_y, s_z)$, $R1(\theta_x, \theta_y, \theta_z)$, $T1(t_x, t_y, t_z)$, $S2(s_x, s_y, s_z)$, $R2(\theta_x, \theta_y, \theta_z)$, and $T2(t_x, t_y, t_z)$ calculated by the registration unit 23, thereby generating the normalized brain image Bd0.

Figure 7:
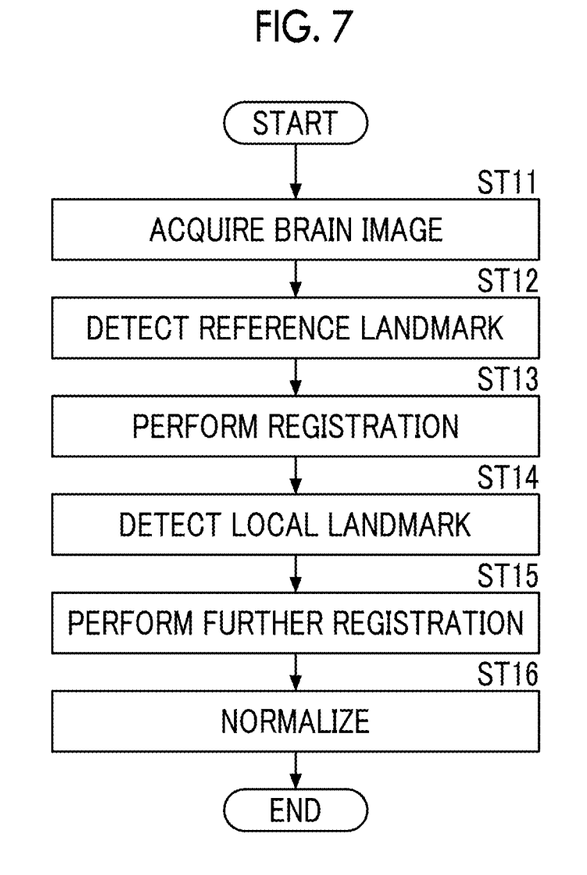
FIG. 7 is a flowchart showing the process performed in a second embodiment.

Next, the process performed in the second embodiment will be described. FIG. 7 is a flowchart showing the process performed in the second embodiment. In the flowchart shown in FIG. 7, the generation of the discriminator 30 and the learning process in the learning unit 31 are omitted. First, the image acquisition unit 21 acquires the brain image B0 to be normalized (step ST11). Then, the landmark detection unit 22 detects at least four reference landmarks among the left eye, the right eye, the diencephalon, the fornix, the corpus callosum, the left hippocampus, and the right hippocampus from the brain image B0 (step ST12).

Then, the registration unit 23 performs registration between the reference landmark detected by the landmark detection unit 22 and the reference landmark corresponding to the detected reference landmark in the standard brain image Bs (step ST13). Then, the landmark detection unit 22 detects a local landmark from the brain image B0 based on the result of registration using the reference landmark (step ST14).

Then, the registration unit 23 performs registration between the reference landmark and the local landmark detected by the landmark detection unit 22 and the reference landmark and the local landmark corresponding to the detected reference landmark and local landmark in the standard brain image Bs (step ST15). Then, the normalization unit 24 normalizes the brain image B0 based on the result of further registration (step ST16), and ends the process.

In the first embodiment described above, the registration between the reference landmark detected from the brain image B0 and the reference landmark in the standard brain image Bs is performed by similarity transformation. However, the registration may be performed by nonlinear transformation. As the registration by nonlinear transformation, for example, there is registration performed by nonlinearly converting pixel positions using functions, such as B spline and thin plate spline. Also in the second embodiment, the registration between the reference landmark and the local landmark detected from the brain image B0 and the reference landmark and the local landmark in the standard brain image Bs may be performed by nonlinear transformation.

In the first and second embodiments described above, after performing registration, additional registration for matching the entire brain image B0, that is, the shape and size of the brain image B0 with the shape and size of the standard brain image Bs may be further performed. In the additional registration, the registration unit 23 calculates an additional coefficient for matching the shape and size of the brain image B0 with the shape and size of the standard brain image Bs. In this case, the normalization unit 24 normalizes the brain image B0 by further using the additional coefficient. In this manner, it is possible to accurately normalize the shape and size of the brain in addition to the anatomical region included in the brain image B0.

In the embodiments described above, the MRI image of the subject is used as a brain image. However, medical images other than the MRI image, such as a CT image and a PET image, may be used as brain images.

Hereinafter, the effect of the present embodiment will be described.

By detecting the reference landmark by performing template matching between the brain image and the template including the reference landmark in the standard brain image, it is possible to accurately detect the reference landmark.

By further detecting at least one local landmark from the brain image based on the registration result, performing further registration between the detected reference landmark and the detected local landmark and a reference landmark and a local landmark corresponding to the detected reference landmark and the detected local landmark included in the standard brain image, and normalizing the brain image based on the result of further registration, it is possible to accurately normalize the brain.

By performing additional registration between the entire brain image and the entire standard brain image after registration, it is also possible to accurately normalize the shape and size of the brain in addition to at least four anatomical regions of the left eye, the right eye, the diencephalon, the fornix, the corpus callosum, the left hippocampus, and the right hippocampus included in the brain and its periphery.

EXPLANATION OF REFERENCES

1: brain image normalization apparatus
2: three-dimensional image capturing apparatus
3: image storage server
4: network
11: CPU
12: memory
13: storage
14: display
15: input unit
21: image acquisition unit
22: landmark detection unit
23: registration unit
24: normalization unit
30: discriminator
31: learning unit
B1 to B3: brain image
Bd1 to Bd3: normalized brain image
Bs: standard brain image
Fs1 to Fs4: local landmark
G1 to G3, Gs: slice image

What is claimed is:

1. A brain image normalization apparatus, comprising a processor configured to:
   detect at least four reference landmarks of a left eye, a right eye, a diencephalon, a fornix, a corpus callosum, a left hippocampus, and a right hippocampus from a brain image including a brain of a subject;
   perform registration between the detected reference landmarks and reference landmarks corresponding to the detected reference landmarks included in a standard brain image, wherein the standard brain image is associated with a brain image of at least one predetermined person; and
   normalize the brain image comprising the detected reference landmarks based on a result of the registration.

2. The brain image normalization apparatus according to claim 1,
   wherein the processor configured to detect the reference landmarks by performing template matching between the brain image and a template including the reference landmarks in the standard brain image.

3. The brain image normalization apparatus according to claim 1,
   wherein the processor further configured to:
   detect at least one local landmark from the brain image based on the registration result;
   perform further registration between the detected reference landmarks and the detected local landmark and reference landmarks and a local landmark corresponding to the detected reference landmarks and the detected local landmark included in the standard brain image; and
   normalize the brain image based on a result of the further registration.

4. The brain image normalization apparatus according to claim 2,
   wherein the processor further configured to:
   detect at least one local landmark from the brain image based on the registration result;
   perform further registration between the detected reference landmarks and the detected local landmark and reference landmarks and a local landmark corresponding to the detected reference landmarks and the detected local landmark included in the standard brain image; and
   normalize the brain image based on a result of the further registration.

5. The brain image normalization apparatus according to claim 1,
   wherein the processor configured to perform the registration by similarity transformation.

6. The brain image normalization apparatus according to claim 2,
   wherein the processor configured to perform the registration by similarity transformation.

7. The brain image normalization apparatus according to claim 3,
wherein the processor configured to perform the registration by similarity transformation.

8. The brain image normalization apparatus according to claim 4,
wherein the processor configured to perform the registration by similarity transformation.

9. The brain image normalization apparatus according to claim 1,
wherein the processor configured to perform the registration by nonlinear transformation.

10. The brain image normalization apparatus according to claim 2,
wherein the processor configured to perform the registration by nonlinear transformation.

11. The brain image normalization apparatus according to claim 3,
wherein the processor configured to perform the registration by nonlinear transformation.

12. The brain image normalization apparatus according to claim 4,
wherein the processor configured to perform the registration by nonlinear transformation.

13. The brain image normalization apparatus according to claim 1,
wherein the processor configured to perform additional registration between the entire brain image and the entire standard brain image after the registration.

14. The brain image normalization apparatus according to claim 2,
wherein the processor configured to perform additional registration between the entire brain image and the entire standard brain image after the registration.

15. The brain image normalization apparatus according to claim 3,
wherein the processor configured to perform additional registration between the entire brain image and the entire standard brain image after the registration.

16. The brain image normalization apparatus according to claim 4,
wherein the processor configured to perform additional registration between the entire brain image and the entire standard brain image after the registration.

17. The brain image normalization apparatus according to claim 5,
wherein the processor configured to perform additional registration between the entire brain image and the entire standard brain image after the registration.

18. The brain image normalization apparatus according to claim 6,
wherein the processor configured to perform additional registration between the entire brain image and the entire standard brain image after the registration.

19. A brain image normalization method, comprising:

detecting at least four reference landmarks of a left eye, a right eye, a diencephalon, a fornix, a corpus callosum, a left hippocampus, and a right hippocampus from a brain image including a brain of a subject;

performing registration between the detected reference landmarks and reference landmarks corresponding to the detected reference landmarks included in a standard brain image, wherein the standard brain image is associated with a brain image of at least one predetermined person; and normalizing the brain image comprising the detected reference landmarks based on a result of the registration.

20. A non-transitory computer readable medium for storing a brain image normalization program causing a computer to execute:

detecting at least four reference landmarks of a left eye, a right eye, a diencephalon, a fornix, a corpus callosum, a left hippocampus, and a right hippocampus from a brain image including a brain of a subject;

performing registration between the detected reference landmarks and reference landmarks corresponding to the detected reference landmarks included in a standard brain image, wherein the standard brain image is associated with a brain image of at least one predetermined person; and normalizing the brain image comprising the detected reference landmarks based on a result of the registration.

* * * * *